US009217881B2

(12) United States Patent
Pugh et al.

(10) Patent No.: US 9,217,881 B2
(45) Date of Patent: Dec. 22, 2015

(54) APPARATUS FOR PROGRAMMING AN ENERGIZABLE OPHTHALMIC LENS WITH A PROGRAMMABLE MEDIA INSERT

(71) Applicant: Johnson & Johnson Vision Care, Inc., Jacksonville, FL (US)

(72) Inventors: Randall B. Pugh, St. Johns, FL (US); Sharika Snook, St. Augustine, FL (US); Camille Higham, Jacksonville, FL (US); Karson S. Putt, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 268 days.

(21) Appl. No.: 13/905,767

(22) Filed: May 30, 2013

(65) Prior Publication Data
US 2014/0354943 A1 Dec. 4, 2014

(51) Int. Cl.
G02B 7/04 (2006.01)
G02C 7/02 (2006.01)
G02C 7/04 (2006.01)
G02C 7/08 (2006.01)
A61F 2/16 (2006.01)

(52) U.S. Cl.
CPC ... *G02C 7/022* (2013.01); *G02C 7/04* (2013.01); *G02C 7/083* (2013.01); *A61F 2/1624* (2013.01)

(58) Field of Classification Search
CPC ........... G02C 7/04; G02C 11/10; G02C 7/083
USPC .................. 351/159.02, 159.03, 159.25
See application file for complete search history.

(56) References Cited

U.S. PATENT DOCUMENTS

| | | |
|---|---|---|
| 2006/0095128 A1 | 5/2006 | Blum et al. |
| 2009/0204250 A1 | 8/2009 | Potyrailo et al. |
| 2009/0206498 A1 | 8/2009 | Tepedino, Jr. et al. |
| 2011/0084834 A1 | 4/2011 | Sabeta |

OTHER PUBLICATIONS

Babak A. Parviz. For Your Eyes Only. (IEEE Spectrum) Sep. 2009.*
Lingley et al. A Single-Pixel Wireless Contact Lens Display. Published Nov. 22, 2011.*
PCT International Search Report for PCT/US2014/839516 Dated Sep. 22, 2014.

* cited by examiner

*Primary Examiner* — Hung Dang (57) ABSTRACT

The present invention discloses an apparatus for programming an energizable Ophthalmic Lens with a programmable Media Insert. In some embodiments, a Media Insert may be programmable to allow for further customization of the energized Ophthalmic Lens. The programming may occur after the electrical components have been encapsulated in the programmable Media Insert. In some embodiments, the apparatus may wirelessly program the Media Insert after the Ophthalmic Lens has been fully assembled. Alternatively, the apparatus may indirectly program the Media Insert by wirelessly programming an overlay. The overlay may subsequently program the Media Insert when placed in proximity to the Media Insert, wherein the placing completes the assembly of the Ophthalmic Lens.

20 Claims, 6 Drawing Sheets

APPARATUS FOR PROGRAMMING AN ENERGIZABLE OPHTHALMIC LENS WITH A PROGRAMMABLE MEDIA INSERT

FIELD OF USE

This invention describes methods, apparatus, and devices related to programming an energizable Ophthalmic Lens with a programmable Media Insert. More specifically, this invention describes a programming apparatus capable of wirelessly programming an assembled energizable Ophthalmic Lens and programmable Media Insert.

BACKGROUND

Traditionally, an Ophthalmic Device, such as a contact lens, an intraocular lens, or a punctal plug included a biocompatible device with a corrective, cosmetic, or therapeutic quality. A contact lens, for example, can provide one or more of vision correcting functionality, cosmetic enhancement, and therapeutic effects. Each function is provided by a physical characteristic of the lens. A design incorporating a refractive quality into a lens can provide a vision corrective function. A pigment incorporated into the lens can provide a cosmetic enhancement. An active agent incorporated into a lens can provide a therapeutic functionality. Such physical characteristics may be accomplished without the lens entering into an energized state.

More recently, active components have been included in a contact Lens, and the inclusion may involve the incorporation of energizing elements within the Ophthalmic Device. The relatively complicated components to accomplish this effect may derive improved characteristics by including them in insert devices which are then included with standard or similar materials useful in the fabrication of state of the art Ophthalmic Lenses.

The inclusion of active components in an Ophthalmic Lens broadens the potential functionalities of the Ophthalmic Lens. With an increased range of functionalities, customization may become more significant but also more complex. Accordingly, new means of personalizing energizable Ophthalmic Lens may be necessary.

It may be desirable to improve the process, methods, and resulting devices for realizing event coloration mechanisms of various kinds. It may be anticipated that some of the solutions for event coloration mechanisms in energizable Ophthalmic Lenses may provide novel aspects for non-energized devices and other biomedical devices. Accordingly novel methods, devices, and apparatus relating to programming and manufacturing an energized Ophthalmic Lens with a programmable Media Insert are therefore important.

SUMMARY

Accordingly, the present invention includes innovations relating to a programming apparatus for programming a first energizable Ophthalmic Lens, the programming apparatus comprising a programming portion capable of wirelessly programming a programmable Media Insert when the programming portion is located in proximity to a first energizable Ophthalmic Lens, wherein the first energizable Ophthalmic Lens comprises the programmable Media Insert and a soft lens base, wherein the soft lens base is in contact with at least a portion of the programmable Media Insert.

In some embodiments, the apparatus may further comprise a power source in electrical communication with the programming portion, and a receiving portion, capable of receiving the first energizable Ophthalmic Lens. The apparatus may be handheld or portable. The receiving portion may comprise an alignment feature, wherein the alignment feature is capable of orienting the first energizable Ophthalmic Lens with the programming portion.

The programming apparatus may further comprise a dispensing portion, wherein the dispensing portion is capable of accessing a plurality of unprogrammed energizable Ophthalmic Lenses with programmable Media Inserts, wherein the first energizable Ophthalmic Lens comprises a selection from the plurality of unprogrammed energizable Ophthalmic Lenses, and wherein the dispensing portion is capable of placing the first energizable Ophthalmic Lens in proximity to the programming portion.

In some embodiments, the programming portion may comprise a receiver capable of receiving programming parameter data; a transmitter capable of wirelessly transmitting a set of programming parameters to the programmable Media Insert; and a processor comprising executable software, wherein the processor is in logical communication with the receiver and the transmitter, and wherein the executable software is capable of storing the set of programming parameters.

The programming apparatus may comprise a programming overlay capable of fitting over the first energizable Ophthalmic Lens, wherein the programming overlay further comprises a soft lens portion capable of encapsulating the receiver, the transmitter, and the processor.

A stock-keeping unit may comprise the set of programming parameters, wherein the programming apparatus further comprises a scanning portion in electrical communication with the receiver and the power source, wherein the scanning portion is capable of recognizing the stock-keeping unit and transmitting the set of programming parameters to the receiver. The receiver may be capable of logical communication with an external device.

In some embodiments, the receiver may comprise an input portion, wherein the input portion may be capable of accepting the set of programming parameters. Alternatively, the receiver may be capable of wirelessly receiving predefined data from the programmable Media Insert of the first energizable Ophthalmic Lens, wherein the programmable Media Insert is capable of collecting the predefined data.

In some embodiments, the programming portion may be capable of programming the programmable Media Insert when the energizable Ophthalmic Lens is located within a sealed container. The sealed container may comprise a reservoir of aqueous solution capable of maintaining a specified level of hydration in the energized Ophthalmic Lens; a rigid portion comprising a recess capable of containing the reservoir and the energized Ophthalmic Lens; and a sealing layer covering the recess, wherein the sealing layer is capable of limiting exposure of the first energizable Ophthalmic Lens to predefined ambient conditions. In some embodiments, the sealing layer may be permeable to a wireless transmission between the transmitter and the programmable Media Insert.

In some embodiments, the stock-keeping unit may be identifiable by a stock-keeping unit barcode located on a surface of the first energizable Ophthalmic Lens or a surface of a container capable of holding the first energizable Ophthalmic Lens. The scanning portion may comprise a light source, such as, for example, a laser, proximate to the stock-keeping unit barcode, wherein the light source is capable of directing light to the stock-keeping unit barcode, and wherein the surface is capable of reflecting the light; and a photodiode that is capable of measuring the intensity of the reflected light.

In some embodiments, the executable software may be capable of adjusting the set of programming parameters based on the predefined data. The programming portion may be capable of wirelessly programming a second energizable Ophthalmic Lens based on the adjusted set of programming parameters. Alternatively, the programming portion may be capable of wirelessly reprogramming the first energizable Ophthalmic Lens based on the adjusted set of programming parameters.

DETAILED DESCRIPTION OF THE INVENTION

The present invention describes a programming apparatus for programming an energized Ophthalmic Lens with a programmable Media Insert. In general, according to some embodiments of the present invention, a programmable Media Insert may be incorporated with an energizable Ophthalmic Lens.

In the following sections, detailed descriptions of embodiments of the invention will be given. The description of both preferred and alternative embodiments are exemplary embodiments only, and it is understood that to those skilled in the art that variations, modifications, and alterations may be apparent. It is therefore to be understood that said exemplary embodiments do not limit the scope of the underlying invention.

GLOSSARY

In this description and claims directed to the presented invention, various terms may be used for which the following definitions will apply:

Adhesion Promoter: as used herein refers to a material or process that increases the adhesiveness of the Rigid Insert to an encapsulant.

Back Curve Piece or Back Insert Piece: as used herein refers to a solid element of a Multi-Piece Insert that, when assembled into the said insert, will occupy a location on the side of the Ophthalmic Lens that is on the back. In an ophthalmic device, such a piece would be located on the side of the insert that would be closer to the wearer's eye surface. In some embodiments, the Back Curve Piece may contain and include a region in the center of an ophthalmic device through which light may proceed into the wearer's eye. This region may be called an Optical Zone. In other embodiments, the piece may take an annular shape where it does not contain or include some or all of the regions in an Optical Zone. In some embodiments of an ophthalmic insert, there may be multiple Back Curve Pieces, and one of them may include the Optical Zone, while others may be annular or portions of an annulus.

Component: as used herein refers to a device capable of drawing electrical current from an Energy Source to perform one or more of a change of logical state or physical state.

Deposit: as used herein refers to any application of material, including, for example, a coating or a film.

Disinfecting Radiation: as used herein refers to a frequency and intensity of radiation sufficient to kill unwanted life forms by receiving a Disinfecting Radiation Dose.

Disinfecting Radiation Dose: as used herein refers to an amount of radiation to reduce an amount of life forms by at least two logs on a logarithmic scale and preferably three logs or more, wherein life forms include at least bacteria, viruses, molds, and fungi.

Electrical Communication: as used herein refers to being influenced by an electrical field. In the case of conductive materials, the influence may result from or in the flow of electrical current. In other materials, it may be an electrical potential field that causes an influence, such as the tendency to orient permanent and induced molecular dipoles along field lines as an example.

Encapsulate: as used herein refers to creating a barrier to separate an entity, such as, for example, a Media Insert, from an environment adjacent to the entity.

Encapsulant: as used herein refers to a layer formed surrounding an entity, such as, for example, a Media Insert, that creates a barrier to separate the entity from an environment adjacent to the entity. For example, Encapsulants may be comprised of silicone hydrogels, such as Etafilcon, Galyfilcon, Narafilcon, and Senofilcon, or other hydrogel contact lens material. In some embodiments, an Encapsulant may be semipermeable to contain specified substances within the entity and preventing specified substances, such as, for example, water, from entering the entity.

Energized: as used herein refers to the state of being able to supply electrical current to or to have electrical Energy stored within.

Energy: as used herein refers to the capacity of a physical system to do work. Many uses within this invention may relate to the said capacity of being able to perform electrical actions in doing work.

Energy Harvesters: as used herein refers to devices capable of extracting Energy from the environment and converting it to electrical Energy.

Energy Source: as used herein refers to any device or layer that is capable of supplying Energy or placing a logical or electrical device in an Energized state.

Event: as used herein refers to a defined set of parameters, such as, for example, a biomarker level, energization level, pH level, or a visual recognition of a particular object. An event may be specific to a wearer, such as a level of medication, or may be generally applicable to all wearers, such as temperature.

Front Curve Piece or Front Insert Piece: as used herein refers to a solid element of a multi-piece Rigid Insert or Media Insert that, when assembled into the said insert, will occupy a location on the side of the Ophthalmic Lens that is on the front. In an ophthalmic device, such a piece would be located on the side of the insert that would be further from the wearer's eye surface. In some embodiments, the piece may contain and include a region in the center of an ophthalmic device through which light may proceed into the wearer's eye. This region may be called an Optical Zone. In other embodiments, the piece may take an annular shape where it does not contain or include some or all of the regions in an Optical Zone. In some embodiments of an ophthalmic insert, there may be multiple Front Curve Pieces, and one of them may include the Optical Zone, while others may be annular or portions of an annulus.

Functionalized: as used herein refers to making a layer or device able to perform a function including for example, energization, activation, or control.

Insert Piece: as used herein refers to a solid element of a multi-piece Rigid Insert or Media Insert that may be assembled into the Rigid Insert or Media Insert. In an Ophthalmic Device, an Insert Piece may contain and include a region in the center of an Ophthalmic Device through which light may proceed into the user's eye. This region may be called an Optic Zone. In other embodiments, the piece may take an annular shape where it does not contain or include some or all of the regions in an Optical Zone. In some embodiments, a Rigid Insert or Media Insert may comprise multiple Inserts Pieces, wherein some Insert Pieces may include the Optic Zone and other Insert Pieces may be annular or portions of an annulus.

Ophthalmic Lens or Ophthalmic Device or Lens: as used herein refers to any device that resides in or on the eye, in contrast to an eyeglass lens. The device may provide optical correction, may be cosmetic, or provide some functionality unrelated to optic quality. For example, the term Lens may refer to a contact Lens, intraocular Lens, overlay Lens, ocular insert, optical insert, or other similar device through which vision is corrected or modified, or through which eye physiology is cosmetically enhanced (e.g. iris color) without impeding vision. Alternatively, Lens may refer to a device that may be placed on the eye with a function other than vision correction, such as, for example, monitoring of a constituent of tear fluid or means of administering an active agent. In some embodiments, the preferred Lenses of the invention may be soft contact Lenses that are made from silicone elastomers or hydrogels, which may include, for example, silicone hydrogels and fluorohydrogels.

Lens-forming Mixture or Reactive Mixture or RMM: as used herein refer to a monomeric composition and/or prepolymer material that may be cured and cross-linked or cross-linked to form an ophthalmic Lens. Various embodiments may include Lens-forming mixtures with one or more additives such as UV blockers, tints, diluents, photoinitiators or catalysts, and other additives that may be useful in an ophthalmic Lenses such as, contact or intraocular Lenses.

Lens-Forming Surface: as used herein refers to a surface that can be used to mold a Lens. In some embodiments, any such surface can have an optical quality surface finish, which indicates that it is sufficiently smooth and formed so that a Lens surface fashioned by the polymerization of a Lens forming material in contact with the molding surface is optically acceptable. Further, in some embodiments, the Lens-forming Surface may have a geometry that may be necessary to impart to the Lens surface the desired optical characteristics, including, for example, spherical, aspherical and cylinder Power, wave front aberration correction, and corneal topography correction.

Liquid Crystal: as used herein refers to a state of matter having properties between a conventional liquid and a solid crystal. A Liquid Crystal cannot be characterized as a solid but its molecules exhibit some degree of alignment. As used herein, a Liquid Crystal is not limited to a particular phase or structure, but a Liquid Crystal may have a specific Resting Orientation. The orientation and phases of a Liquid Crystal may be manipulated by external forces such as, for example, temperature, magnetism, or electricity, depending on the class of Liquid Crystal.

Media Insert: as used herein refers to an encapsulated insert that will be included in an energized ophthalmic device. The energization elements and circuitry may be embedded in the Media Insert. The Media Insert defines the primary purpose of the energized ophthalmic device. For example, in embodiments where the energized ophthalmic device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose or administering medicine.

Mold: as used herein refers to a rigid or semi-rigid object that may be used to form Lenses from uncured formulations. Some preferred Molds include two Mold parts forming a front curve Mold part and a back curve Mold part, each Mold part having at least one acceptable Lens-Forming Surface.

Optic Zone: as used herein refers to an area of an ophthalmic Lens through which a user of the ophthalmic Lens sees.

Precure: as used herein refers to a process that partially cures a mixture. In some embodiments, a precuring process may comprise a shortened period of the full curing process. Alternatively, the precuring process may comprise a unique process, for example, by exposing the mixture to different temperatures and wavelengths of light than may be used to fully cure the material.

Predose: as used herein refers to the initial deposition of material in a quantity that is less than the full amount that may be necessary for the completion of the process. For example, a predose may include a quarter of the necessary substance.

Postdose: as used herein refers to a deposition of material in the remaining quantity after the predose that may be necessary for the completion of the process. For example, where the predose includes a quarter of the necessary substance, a subsequent postdose may provide the remaining three quarters of the substance.

Power: as used herein refers to work done or Energy transferred per unit of time.

Rechargeable or Re-energizable: as used herein refers to a capability of being restored to a state with higher capacity to do work. Many uses within this invention may relate to the capability of being restored with the ability to flow electrical current at a certain rate for certain, reestablished time periods.

Reenergize or Recharge: as used herein refers to restoring to a state with higher capacity to do work. Many uses within this invention may relate to restoring a device to the capability to flow electrical current at a certain rate for certain, reestablished time periods.

Released or Released from a Mold: as used herein refers to a Lens that is either completely separated from the Mold or is only loosely attached so that it may be removed with mild agitation or pushed off with a swab.

Storage Mode: as used herein refers to a state of a system comprising electronic components where a power source is supplying or is required to supply a minimal designed load current. This term is not interchangeable with Standby Mode.

Three-dimensional Surface or Three-dimensional Substrate: as used herein refers to any surface or substrate that has been three-dimensionally formed where the topography is designed for a specific purpose, in contrast to a planar surface.

Trace: as used herein refers to a battery component capable of electrically connecting the circuit components. For example, circuit Traces may include copper or gold when the substrate is a printed circuit board and may be copper, gold, or printed Deposit in a flex circuit. Traces may also be comprised of nonmetallic materials, chemicals, or mixtures thereof.

Variable Optic: as used herein refers to the capacity to change an optical quality, such as, for example, the optical power of a lens or the polarizing angle.

Ophthalmic Lens

Figure 1:
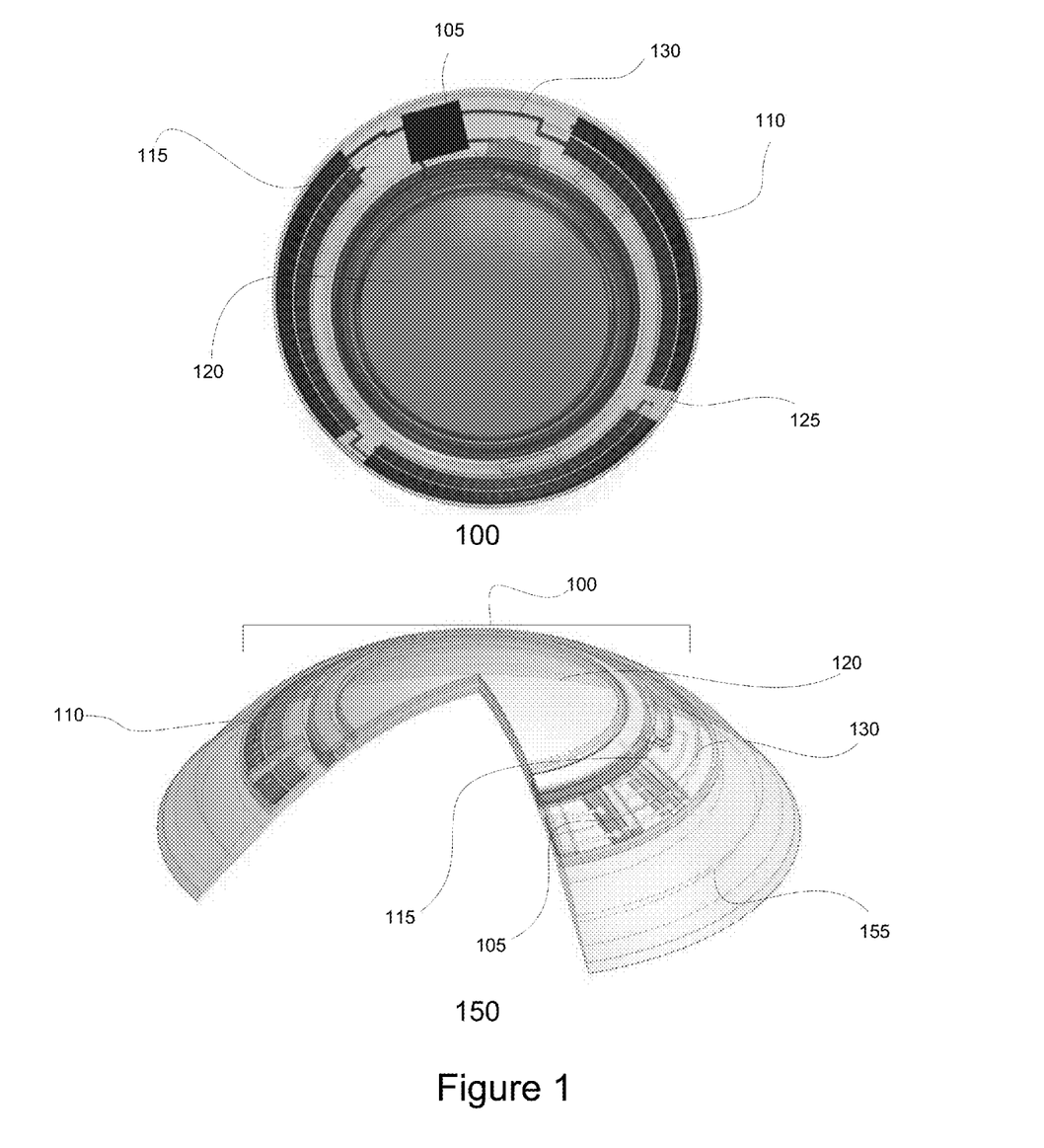
FIG. 1 illustrates an exemplary embodiment of a Media Insert for an energized Ophthalmic Lens and an exemplary embodiment of an energized Ophthalmic Lens.

Proceeding to FIG. 1, an exemplary embodiment of a Media Insert 100 for an energized Ophthalmic Device and a corresponding energized Ophthalmic Device 150 are illustrated. The Media Insert 100 may comprise an Optical Zone 120 that may or may not be functional to provide vision correction. Where the energized function of the Ophthalmic Device is unrelated to vision, the Optical Zone 120 of the Media Insert 100 may be void of material. In some embodiments, the Media Insert 100 may include a portion not in the Optical Zone 120 comprising a substrate 115 incorporated with energization elements 110 and electronic components 105.

In some embodiments, a power source 110, which may be, for example, a battery, and a load 105, which may be, for example, a semiconductor die, may be attached to the substrate 115. Conductive traces 125 and 130 may electrically interconnect the electronic components 105 and the energization elements 110.

In some embodiments, the electronic components 105 may include a processor, which may be programmed to establish the parameters of the functionality of the Ophthalmic Lens. For example, where the Ophthalmic Lens comprises a variable optic portion in the Optical Zone 120, the processor may be programmed to set the energized optical power. Such an embodiment may allow for mass production of Media Inserts that have the same composition but include uniquely programmed processors.

The processor may be programmed before the encapsulation of the electrical components 105, 130, 110, 125 within the Media Insert. Alternatively, the processor may be programmed wirelessly after encapsulation. Wireless programming may allow for customization after the manufacturing process, for example, through a programming apparatus, which may be portable. For illustrative purposes, the Media Inserts 100 are shown to include a portion in the Optical Zone 120. However, where the functionality of the Media Insert may not be related to vision, the Media Insert may be annular, wherein the components of the Media Insert are outside of the Optical Zone.

The Media Insert 100 may be fully encapsulated to protect and contain the energization elements 110, traces 125 and 130, and electronic components 105. In some embodiments, the encapsulating material may be semi-permeable, for example, to prevent specific substances, such as water, from entering the Media Insert 100 and to allow specific substances, such as ambient gasses or the byproducts of reactions within energization elements, to penetrate or escape from the Media Insert 100.

In some embodiments, the Media Insert 100 may be included in an Ophthalmic Device 150, which may comprise a polymeric biocompatible material. The Ophthalmic Device 150 may include a rigid center, soft skirt design wherein a central rigid optical element comprises the Media Insert 100. In some specific embodiments, the Media Insert 100 may be in direct contact with the atmosphere and the corneal surface on respective anterior and posterior surfaces, or alternatively, the Media Insert 100 may be encapsulated in the Ophthalmic Device 150. The periphery 155 of the Ophthalmic Device 150 may be a soft skirt material, including, for example, a polymerized Reactive Monomer Mixture, such as a hydrogel material.

Figure 2A:
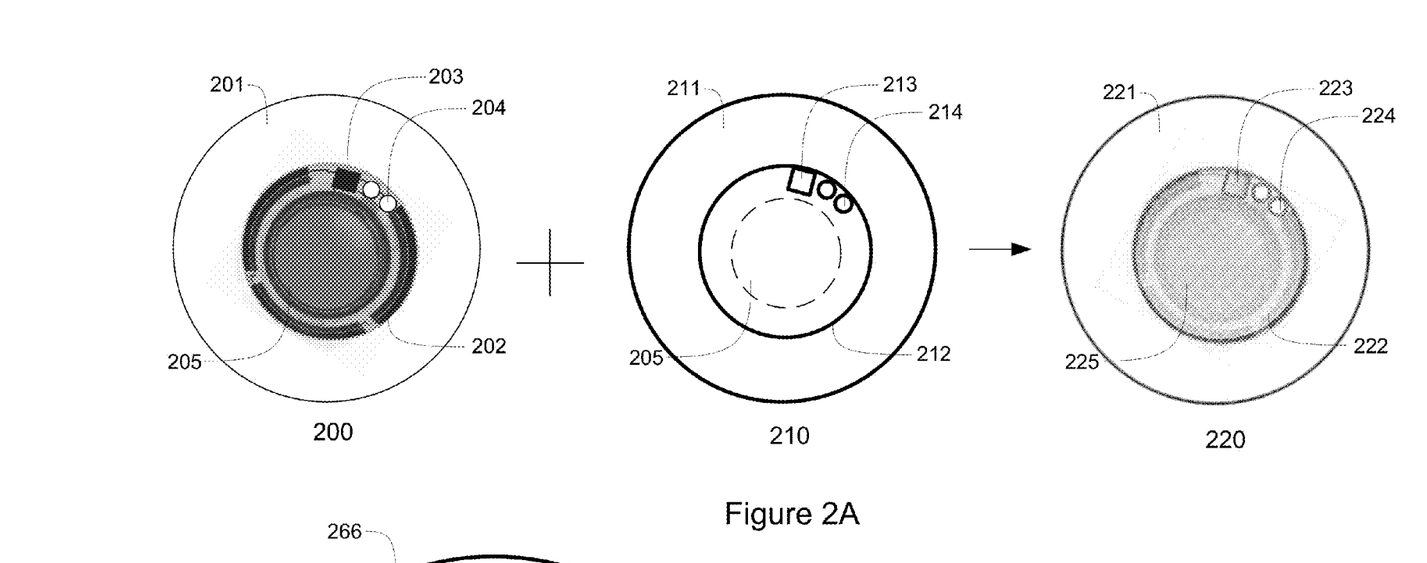
FIG. 2A illustrates a top down view of an exemplary embodiment of an unprogrammed energizable Ophthalmic Lens and a programming overlay.

Proceeding to FIG. 2A, an exemplary unprogrammed energizable Ophthalmic Lens base 200 and a programming overlay 210 are illustrated in a top down view. In some embodiments, an unprogrammed energizable Ophthalmic Lens base 200 may include a soft lens portion 201 and a Media Insert 202, such as, for example, described in FIG. 1. The Media Insert 202 may comprise the materials for the defined functionality. For example, where the Media Insert 202 provides a variable optic functionality, the Media Insert 202 may include a liquid lens or liquid crystal portion 205 in the Optic Zone of the Ophthalmic Lens base 200. Alternatively, the Media Insert 202 may monitor specific constituents in the tear fluid, and the Media Insert 202 may include specific reactants or binding chemicals to quantify the concentration of those constituents.

Prior to programming, the processor 203 of the Media Insert 202 may include the executable software that may allow for functional control, but may not be programmed to the specified parameters for a particular user. For example, where the Media Insert 202 provides a variable optic functionality, the processor 203 may include the executable software necessary to operate the energization of the liquid lens portion 205, but the processor may not be programmed to the varied optic powers.

In its unprogrammed state, the Ophthalmic Lens base 200 may provide a nonenergized functionality, such as, for example, a static vision-correcting power. Such an embodiment may also allow for safe and functional default mode, if, for example, the programming or energization fails. Where a secondary functionality may not be necessary, a malfunctioning Media Insert 202 may default to an optically transparent state, wherein the user's vision may not be impaired.

A programming overlay 210 may comprise a thin biocompatible portion 211, in similar shape, size, and composition to the soft portion 201 of the Ophthalmic Lens base 200. The programming overlay 210 may be capable of programming the Media Insert 202 when placed in proximity to the Ophthalmic Lens base 200. For example, the Ophthalmic Lens base 200 may be placed on the eye, and the user may place the programming overlay 210 on top of the Ophthalmic Lens base 200. Once in proximity to the Media Insert 202, the programming overlay 210 may transmit the programming data to the processor 203 in the Media Insert 202.

In some embodiments, the Media Insert 202 may be fully encapsulated, wherein the encapsulation protects and isolates the components of the Media Insert 202 from the ocular environment, limiting direct contact between the ocular environment and the components, including, for example, electrical components. Accordingly, the programming overlay 210 may be capable of wirelessly communicating with the Media Insert 202. In some embodiments, the Media Insert 202 may further comprise a sensor 204 capable of sensing the proximity of the programming overlay 210 and receiving programming data. Similarly, the programming overlay 210 may further comprise a transmitting sensor 214 capable of sensing the proximity of the Media Insert 202 and transmitting the programming data.

The Media Insert 202 sensor 204 may be in logical communication with the processor 203, and the programming overlay 210 sensor 214 may be in logical communication with the overlay processor 213. When the programming overlay 210 is placed over the Ophthalmic Lens base 200, a programmed Ophthalmic Lens 220 may be formed.

In some embodiments, such as illustrated, the sensors 204, 214 may be directly aligned. The small size of the sensors 204, 214 may make it difficult to align. Accordingly, alignment features may facilitate the orientation between the programming overlay 210 and the Media Insert 202 sensor 204. In some embodiments, the alignment features may be magnetic, wherein the programming overlay 210 may self-align when placed in proximity to the complementary alignment feature on one or both the Ophthalmic Lens base 200 or the programmable Media Insert 202.

In other embodiments, the sensors may be less sensitive and direct alignment may not be required. In such embodiments, alignment may still be significant. For example, an alignment feature 212 may secure the fit between the programming overlay 210 and one or both the Ophthalmic Lens base 200 or the programmable Media Insert 202. The secured positioning may allow for a consistently comfortable fit, and the security may limit movement between the programming overlay 210, Ophthalmic Lens base 200, and the programmable Media Insert 202.

The programming overlay 210 may also include a processor 213, which may be able to store the programmed parameters. The processor 213 may also include executable software capable of controlling the reception and transfer of data, including, for example, the programming parameters. In some embodiments, the executable software in the programming overlay 210 may translate the input programming parameters to an operational code. In other embodiments, the programming overlay 210 may only transmit the programming parameters, and executable software in the Media Insert 202 processor 203 may translate the programming parameters.

Figure 2B:
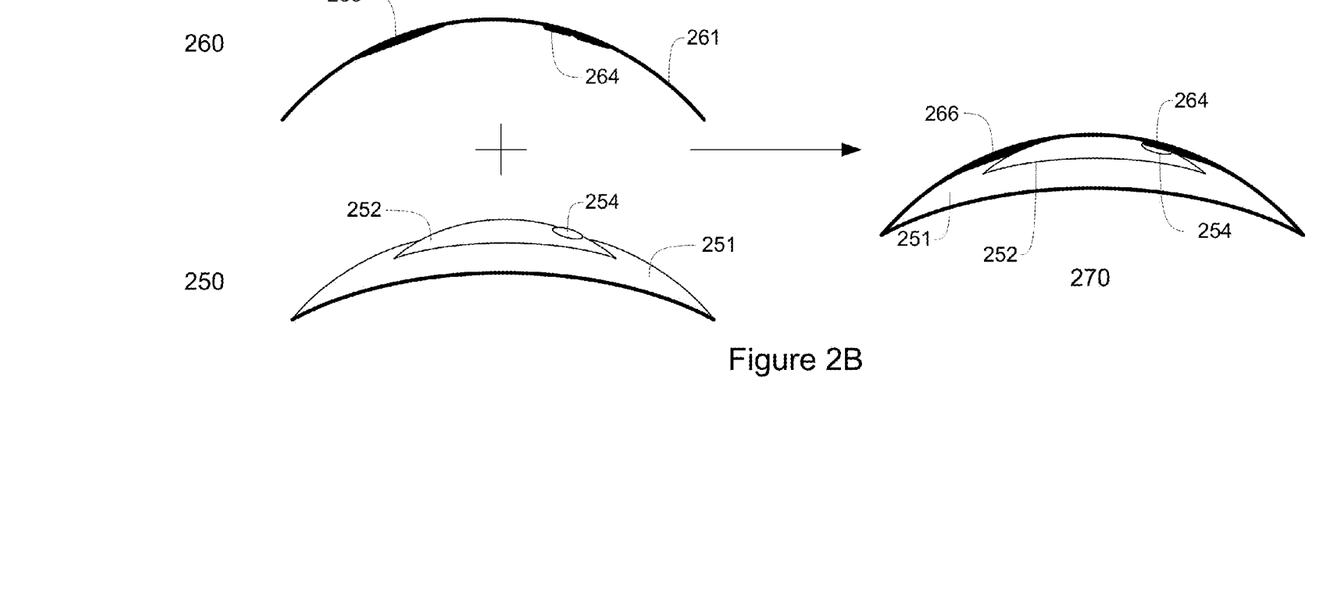
FIG. 2B illustrates a cross sectional view of an exemplary embodiment of an unprogrammed energizable Ophthalmic Lens and a programming overlay.

Proceeding to FIG. 2B, an exemplary unprogrammed energizable Ophthalmic Lens base 250 and a programming overlay 260 are illustrated in cross section. In some embodiments, the Media Insert 252 may not be fully encapsulated by the soft lens portion 251, which may allow a closer proximity between the Media Insert 252 and the programming overlay 260. In such embodiments, the programming overlay 260 may be formed to include a pocket 266 for the portion of the Media Insert 252 not encapsulated by the soft lens portion 251.

In some such embodiments, the Ophthalmic Lens base 250 may include the base prescription, such as would be included in a non-energizable Ophthalmic Lens, and the programmed overlay 260 may be universal. A universal overlay 260 may allow the programmer, such as, for example, the ophthalmologist, to keep a stock of the overlays without committing to specific Ophthalmic Lens base 250, where the demand may be less predictable.

For example, where the programmed Ophthalmic Lens 250 provides variable optic powers for patients with presbyopia, the number of patients with presbyopia may be more predictable than the specific prescription supply demands. The Ophthalmic Lens bases 250 may be ordered based on general demand or the specific demands of an individual patient, but the ophthalmologist may be able to program the overlays before the patient leaves the office.

Secondary alignment features may be necessary in some embodiments, which may allow for a secure complete assembly 270. For example, the sensors 254, 264 may be magnetic. Alternatively, the programmed overlay 260 may mechanically fit with the Ophthalmic Lens base 250, such as through tongue and groove, or a snap fit. In some such embodiments, the fitting mechanisms may not be near the sensors, which may allow for a broader range of alignment mechanisms.

In still further embodiments, the sensors 254, 264 may not require particular circular alignment. For example, the sensors 254, 264 may be sensitive enough to recognize proximity when assembled 270, when the programmed overlay 260 may be placed on the Ophthalmic Lens base 250.

Figure 3:
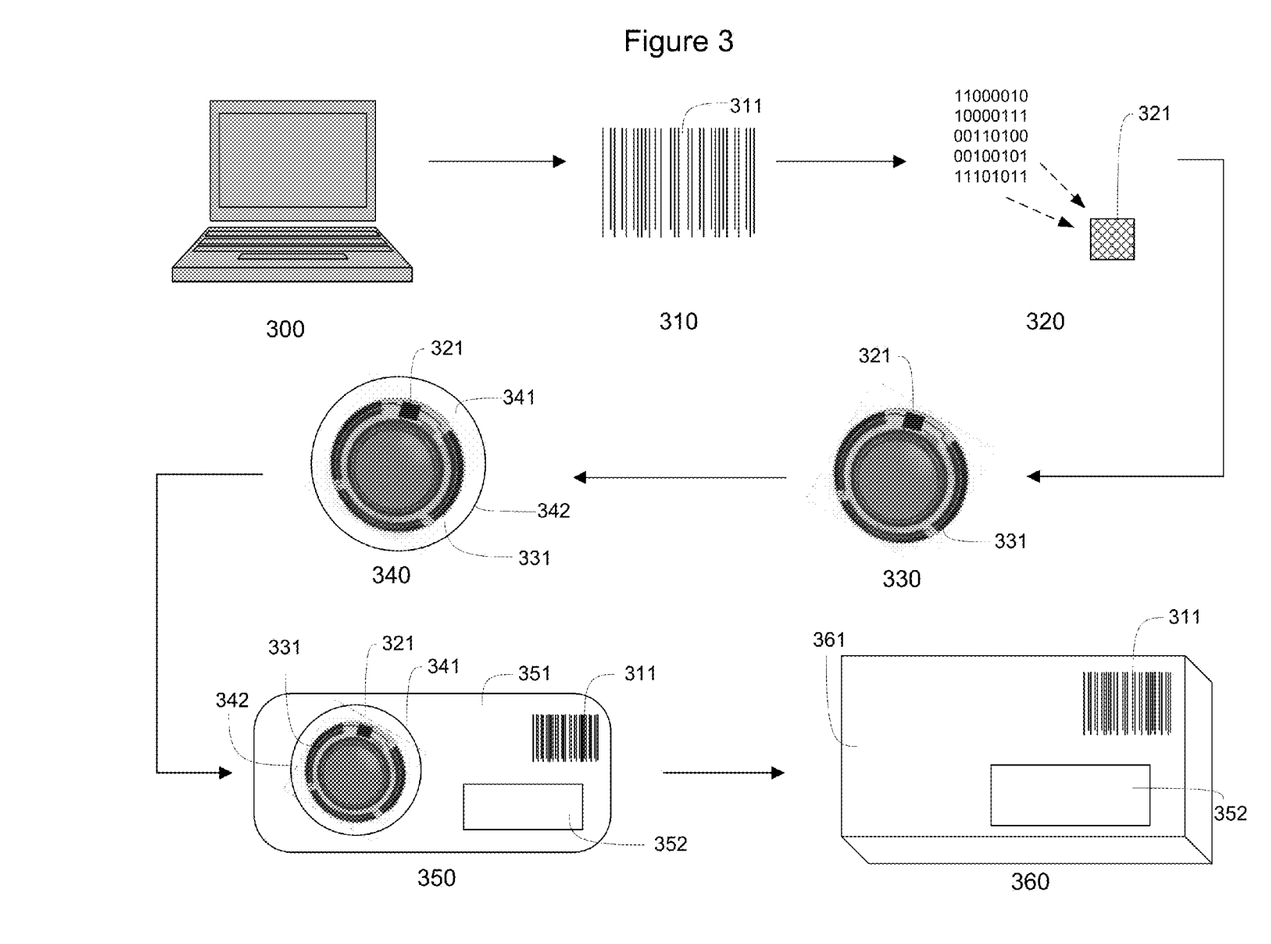
FIG. 3 illustrates an exemplary process flowchart for pre-programming an energizable Ophthalmic Lens.

Proceeding to FIG. 3, an exemplary embodiment of a process flowchart for processing and preprogramming an energizable Ophthalmic Lens 342 is illustrated. In some embodiments, the programming may occur at 320 prior to including the Media Insert 321 in the Ophthalmic Lens 331, at 340. In some such embodiments, the manufacturer may also be the programmer. Alternatively, the processor may be preprogrammed, wherein the programming at 320 may occur separately from the assembly steps, at 330, 340, and the packaging steps, at 350, 360.

As an illustrative example, a doctor, such as an ophthalmologist or physician, may assess a patient to determine the necessary parameters for the energizable Ophthalmic Lens 332. Where the functionality of the Ophthalmic Lens 332 is directly related to the eye, including, for example, vision correction or administering a pain relieving ointment to a post-operative eye, an ophthalmologist may be best suited to define the parameters.

In other cases, such as where the Ophthalmic Lens 342 may be capable of monitoring or treating a specific health condition, doctors other than an ophthalmologist may define the parameters for the Ophthalmic Lens 342. For example, a Media Insert 331 may interact or interface with the ocular environment, such as the tear fluid. In other embodiments, such as where the Ophthalmic Lens provides a primarily cosmetic function, the user may define the parameters.

At 300, the defined parameters may be input, and at 310, a stock-keeping unit (SKU) may be generated unique to those parameters. The defined parameters may be input, at 310, off the manufacturing site, such as, for example, at a doctor's office or a user's home computer. Alternatively, the manufacturer may input the defined parameters, at 300, based on the instructions from a user or someone on behalf of the user.

In some embodiments, the steps at 300 and 310 may occur almost simultaneously, either by the same device or through use of the internet, where a SKU is immediately generated, at 310, once the defined parameters are input, at 300. In others, the SKU may be generated, at 310, once the programming and manufacturing process, at 320-360. At 320, the processor 321 may be programmed according to the defined parameters assigned to the SKU. In some embodiments, the programming, at 320, may occur prior to assembling the Media Insert 331, at 330. In other embodiments, the programming, at 320, may occur as part of the assembly process, at 330.

At 340, the Media Insert 331 may be included in an Ophthalmic Lens 342, such as, for example, by adding a soft skirt portion 341, encapsulating the Media Insert 331 in a soft, biocompatible material 341, or by fitting the Media Insert 331 into a pocket of the soft lens portion 341. Various techniques may be practical depending on method of inclusion. For example, a Media Insert 332 may be encapsulated, at 340, through an injection mold process. Alternatively, the soft lens portion 341 may be formed independently through freeform techniques, such as through exposure to actinic radiation, which may allow the formation of a fitted pocket.

In some embodiments at 350, the programmed Ophthalmic Lens 342 may be further packaged for shipping. The packaging 351 may include the SKU 311 number, such as through a bar code, and a label 352, which may list properties of the programmed Ophthalmic Lens 342, including, for example, size, resting optic power, and energized optic power. For exemplary purposes, the packaging 351 is illustrated as a blister embodiment. Other embodiments may be practical and should be considered part of the inventive art included herein. In some such embodiments, at 360, the packages 351 of Ophthalmic Lenses 342 may be further included in boxes 361, as may be common with traditional non-energized Ophthalmic Lenses. The boxes 361 may include similar markings as the package 351, such as the label 352 and the SKU 311.

A programming method where the programming occurs prior to the encapsulation of the Media Insert 331 may be particularly preferable where customization of other components of the Ophthalmic Lens 342 or Media Insert 331 may be necessary. In some embodiments, the Ophthalmic Lens 342 may further include a colored iris pattern, which may obscure the electronic components and may add a static cosmetic characteristic. The customized color may be manufactured to the specifications of a particular SKU.

Some energizable functionality may depend on a specific substance. For example, monitoring glucose in the tear fluid may depend on a measurable reaction between the glucose and a reactant, such as glucose oxidase. Where the monitored conditions may be customizable, the reactants may need to be customized accordingly. In some such embodiments, acquiring input parameters prior to the completed manufacturing process may be practical.

This embodiment may also limit the need for a programming overlay, which may simplify the process for the user. The Ophthalmic Lens 342 may be fully programmed and fully assembled when packaged at step 350. Accordingly, a further step of placing the overlay on the Ophthalmic Lens base may not be necessary for programming purposes.

Programming Apparatus

Figure 4:
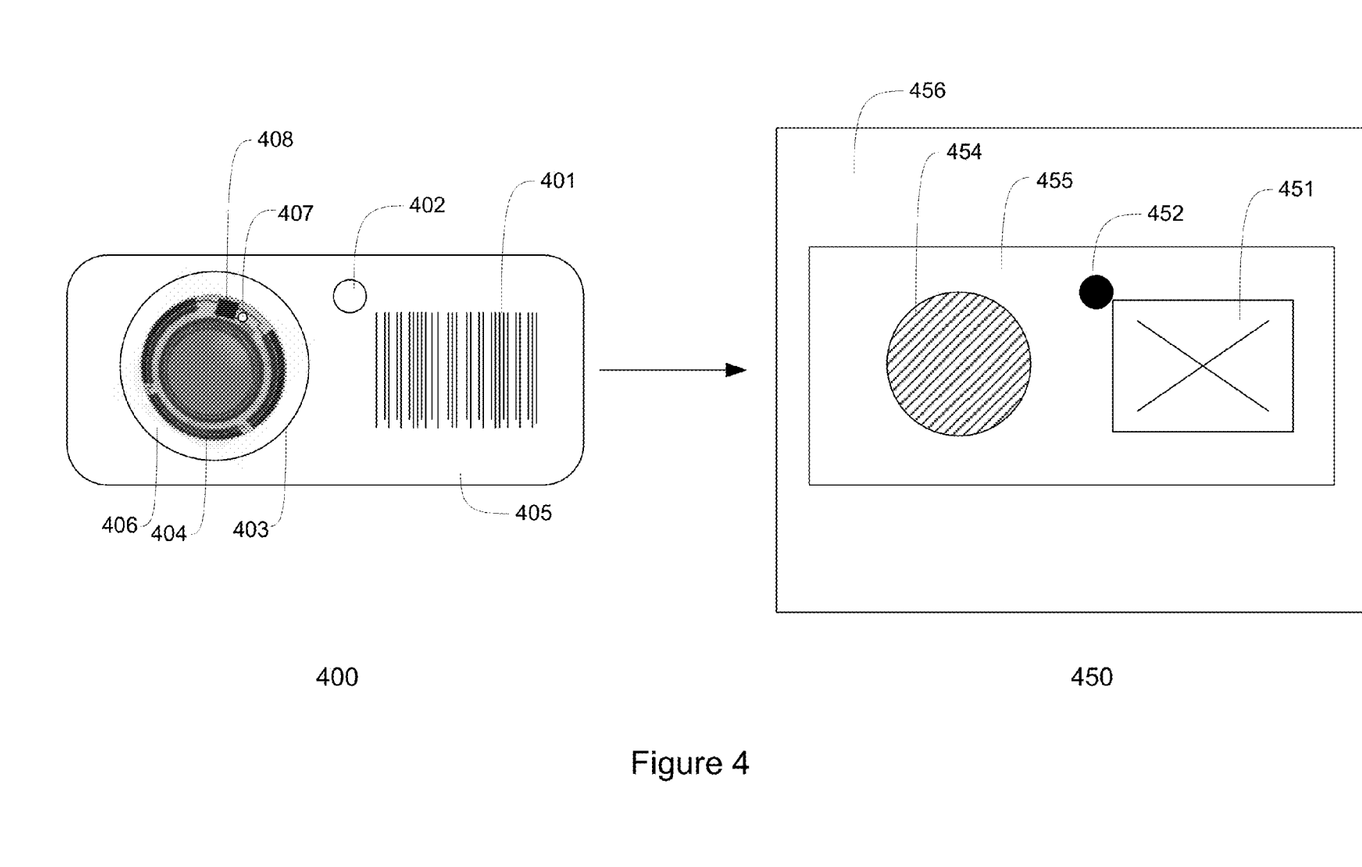
FIG. 4 illustrates an exemplary apparatus for programming an energizable Ophthalmic Lens.

Proceeding to FIG. 4, an exemplary embodiment of a programming apparatus 450 and a programmable Ophthalmic Lens 403 is illustrated. In some embodiments, the Ophthalmic Lens 403 may be stored before use in a container 400, such as, for example, a blister. The container 400 may comprise a sealed plastic 405 with a pocket filled with an aqueous solution to store the Ophthalmic Lens 403. Where the container 400 may interact with a programming apparatus 450, an alignment feature 402 may be able to secure and orient the container 400 within the programming apparatus 450, such as through a complementary alignment feature 452 in the programming apparatus 450.

In some embodiments, the programming apparatus 450 may be opened similar to clam shell, wherein the container 400 may be placed in the aligning recess 455. Alternatively, a container 400 may be inserted through a slot in the programming apparatus 450, wherein the container 400 may be "clicked" into the alignment features 452, 455.

The seal for the container 400 may comprise a material that protects the Ophthalmic Lens 403 from ambient light exposure. In some embodiments, the seal may be removed prior to programming. The removal may reveal an unsealed container or may reveal a more transparent secondary seal. In others, where the programming device 454 within the apparatus 450 may permeate the seal, the removal may not be necessary. It may be preferable to preserve the sterility of the Ophthalmic Lens 403 by programming the Ophthalmic Lens 403 while it is still enclosed in a sterile saline solution. Alternatively, the programming apparatus 450 may include a sterilizing function.

In some embodiments, the container 405 may include a SKU barcode 401 in a scannable portion, for example, on the top as illustrated. The apparatus 450 may be able to scan the SKU barcode 401 on the container 405. Upon recognition, the apparatus 450 may program the Ophthalmic Lens 403 based on the programming parameters associated with the stockkeeping unit. Accordingly, the SKU barcode 401 may be located under a seal that may be removed prior to scanning. Alternatively, the SKU barcode 401 may be embedded in on printed on the Ophthalmic Lens 403, such as on the soft lens portion 406 or the Media Insert 404.

The programmable Ophthalmic Lens 403 may comprise a Media Insert 403 and a soft lens portion 406. The Media Insert 403 may further comprise a receiver or antenna portion 407, which may allow the apparatus 450 to program a processor 403 within a fully encapsulated Media Insert 403. In some embodiments, the soft lens portion 406 may further encapsulate the Media Insert 403. Alternatively, a portion of the soft lens 406 may secure the Media Insert 403 within the Ophthalmic Lens 403. The programming apparatus 450 may comprise a scanning device 451 and a programming device 454.

The scanning device 451 may scan and recognize the SKU barcode 401 on the Ophthalmic Lens 403 or its container 405. The scanning device 451 may communicate electrically and logically with the programming device 454, wherein the scanning device 451 may transmit the SKU data to the programming device 454. In some embodiments, the scanning device 451 may comprise a light source, such as a laser, that may direct light to the SKU barcode 401, and a photodiode that may measure the intensity of the reflected light from the surface of the SKU barcode 401.

In some embodiments, the programming device 454 may comprise a database of the SKU numbers and their corresponding programming parameters. In some other embodiments, the programming device 454 may be connected to an external database, such as through an internet connection or a USB connection to a computer. In still further embodiments, a programming apparatus 450 may be programmed directly, and the SKU barcode 401 scan may serve as a confirmation that the unprogrammed Ophthalmic Lens 403 matches the SKU assigned to the parameters.

The programming apparatus 450 may further comprise an alignment feature 452 that may complement the alignment feature 402 on the container 405. Similarly, the container 405 may fit into a recess or pocket 455, which may help ensure the scanning device 451 and the programming device 454 align with the SKU barcode 401 and the Ophthalmic Lens 403, respectively. Where the container 405 comprises a pocket, the pocket may snap into fitted recess in the programming apparatus 450. The alignment may orient the container 400 within the programming apparatus 450, wherein the sensor 407 may be aligned with the programming device 454 and the SKU barcode 401 may be aligned with the scanning device 451.

In some embodiments, the programming apparatus 450 may comprise a portable device. A portable size may allow a doctor to take the device into examination rooms, without having to reserve space for a permanent programming station within the office. Alternatively, the portable size may allow for a personal programming apparatus 450, wherein a user may operate the programming apparatus 450 outside of a doctor's office, such as, in their home.

In some embodiments, not shown, the programming apparatus may comprise a handheld device. The handheld device may scan and program an Ophthalmic Lens 403 without requiring special placement or alignment. For example, a programmer may manually hold the programming apparatus in proximity to the Ophthalmic Lens 403.

In some embodiments, an ophthalmologist or other doctor may program the programming apparatus 450 to recognize a left and right Ophthalmic Lens 403 based on separate SKU barcodes 401, and the user may be able to operate the apparatus 450. For example, the user may order unprogrammed Ophthalmic Lenses 403 and may program the Ophthalmic Lenses 403 utilizing the programming apparatus 450 as needed. For example, with daily wear Ophthalmic Lenses 403, the user may program a left and a right Ophthalmic Lens 403 daily.

In some embodiments, the Ophthalmic Lens 403 may monitor a defined attribute, such as, for example, ambient light, serotonin in the tear fluid, or temperature of the ocular environment. To effectively treat a patient, a doctor may benefit from the data accumulated by the Ophthalmic Lens 403. In some such embodiments, the programming apparatus 450 may also be able to upload stored data from the Ophthalmic Lens 403 associated with a particular SKU.

After use, a user may be able to place the Ophthalmic Lens 403 back into the programming apparatus 450. In such embodiments, a SKU barcode 401 may be embedded in or printed on the Ophthalmic Lens 403, for example on the surface of the Media Insert 404 or the soft lens portion 406. The inclusion of the SKU barcode 401 in the Ophthalmic Lens 403 instead of or in addition to a SKU barcode 401 included on a container 400 may limit the risk of associating the monitored data with the wrong SKU.

Where the functionality of the Ophthalmic Lens 403 includes a cosmetic aspect, the user may enter the programming parameters. For example, a user may order a set of unprogrammed cosmetic Ophthalmic Lenses 403, wherein the programming may determine the color and design of the cosmetic aspect. In some embodiments, the programming parameters may set a static design and coloration. In other embodiments, the programming parameters may set a limited number of settings, through which the user may cycle while the Ophthalmic Lens 403 is on eye, for example, through a blink detection mechanism.

An Ophthalmic Lens 403 may be limited to a single programming or may be reprogrammed throughout the course of the recommended use. For example, where an Ophthalmic Lens 403 includes a programmable cosmetic attribute, the user may reprogram the coloration and design scheme prior to each use. In some embodiments, the SKU may limit the number of times an Ophthalmic Lens 403 may be programmed. Where the recommended use for an Ophthalmic Lens 403 is thirty days, the Ophthalmic Lens may need to be reprogrammed daily, and may only be reprogrammed thirty times.

In some embodiments, operation times or notifications may be controlled through the programmed parameters, which may prompt the user to take a specific action. For example, where monitored data may need to be uploaded periodically throughout the day, the Ophthalmic Lens 403 may be programmed to trigger a notification to place the Ophthalmic Lens 403 into the programming apparatus 450 for an upload. In some embodiments, the programming device 454 may further comprise executable software that may adjust the programming based on the uploaded data from the Ophthalmic Lens 403.

As an illustrative example, an Ophthalmic Lens 403 may comprise a mechanism for administering light therapy based on a programmed schedule. A doctor may initially set general programming parameters based on the severity of the patient's condition. The doctor may also include a series of schedule factors that may warrant an adjustment in the light schedule. Such factors may include, for example, exposure to ambient light, activity levels, sleep cycles, and serotonin levels. After a specified amount of time, such as one week, the user may place the used Ophthalmic Lens 403 back into the programming apparatus 450, which may then upload the factor data gathered throughout the week. Based on the newly uploaded data, the programming device 454 may adjust the light therapy schedule. Such an embodiment may allow for continual optimization without requiring constant doctor visits.

The programming apparatus 450 may include an independent power source, such as a battery, or may require an external power supply, such as by connecting the programming apparatus 450 to a wall outlet or to a computer. For example, a universal serial bus (USB) connector may allow a computer to charge the programming apparatus 450, upload data from the programming apparatus 450, and download the programming parameters to the programming device 454. Some such embodiments may not require an overlay for programming purposes.

Figure 5:
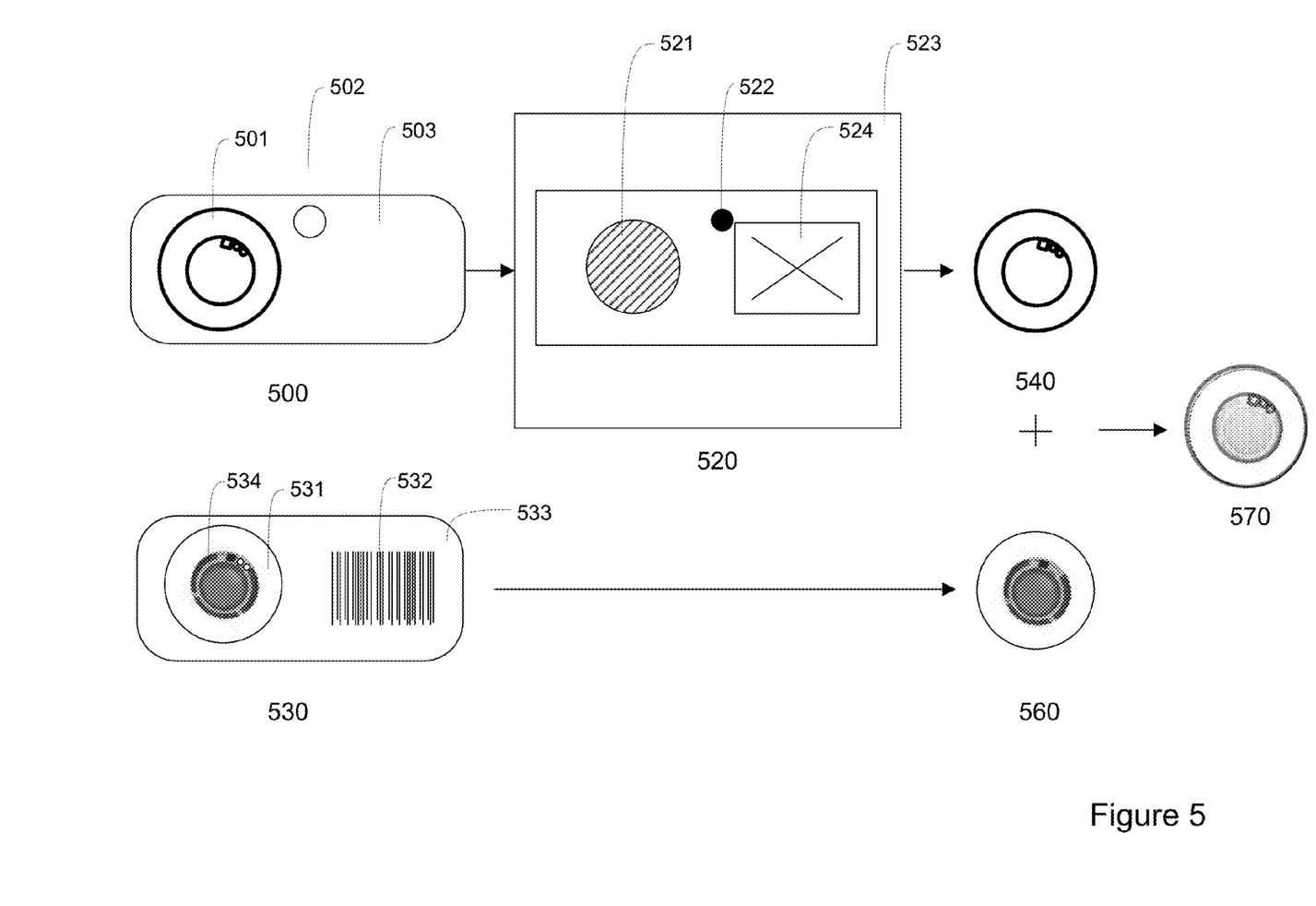
FIG. 5 illustrates an alternative process flowchart for programming an energizable Ophthalmic Lens.

Proceeding to FIG. 5, an embodiment of a programmable Ophthalmic Lens base 531, a programming overlay 501, and a programming apparatus 520 are illustrated. In some embodiments, a programming overlay 501 may be programmed through use of a programming apparatus 520, and the programming overlay 501 may be combined with an Ophthalmic Lens 531 with an unprogrammed Media Insert 534.

A programming overlay 501 may be stored and processed while sealed within a container 500, similar to that described with FIGS. 3 and 4. The container 500 may include an alignment feature 502 that may complement an alignment feature 522 in the programming apparatus 520. In some embodiments, the container 500 may include the SKU barcode, not shown, for example, by printing on the plastic portion 503.

In some embodiments, the container that may include the Ophthalmic Lens base 531 and programmable Media Insert 534 may include the SKU barcode 532 on the plastic portion 533. A scanning portion 524 of the programming apparatus 524 may scan either or both containers 500, 530. Scanning the SKU barcode 532 on one or both the containers 500, 530 may provide confirmation that the correct overlay 501 is being programmed. The SKU barcode 532 may also direct the programming apparatus 520 to pull the programming parameters from a database.

As described with FIG. 4, the container 503 may be inserted or placed within the programming apparatus 520. A programming portion 521 may transmit the programming parameters to the programming overlay 501, for example, through logical communication with the processor or receiving portion.

In some embodiments, the container 500 with the programming overlay 501 may be inserted or placed in the programming apparatus 520. The programming apparatus 520 may include a programming portion 521 that may wirelessly transmit the programming parameters to the programming overlay 501. The programmed programming overlay 540 may be placed over the Ophthalmic Lens base and programmable Media Insert assembly 560.

The placement may complete the formation of the programmed Ophthalmic Lens 570. In some embodiments, the placement may occur prior to placing the Ophthalmic Lens base and programmable Media Insert assembly 560 on the eye. In others, the programming overlay 530 may be placed over the assembly 560 when the assembly 560 is located on the eye.

In some embodiments, the Ophthalmic Lens base 531 and programmable Media Insert 534 may be manufactured based on the programming parameters. For example, a programmable Ophthalmic Lens line may be capable of monitoring a wide range of tear fluid constituents, but a single Ophthalmic Lens 570 may be limited to three constituents. In some such embodiments, the programming parameters may include selecting the three constituents. Accordingly, the Media Insert 534 may be assembled to specifically include reactants to those three constituents.

Alternatively, programming parameter options may be based on the core properties of one or both the Ophthalmic Lens base 531 and the programmable Media Insert 534. For example, where an Ophthalmic Lens line includes a variable optic portion, the Media Inserts may be universal, and the Ophthalmic Lens bases may be offered in a limited range of static optic powers. In such embodiments, customized manufacturing may not be practical or offered.

Figure 6:
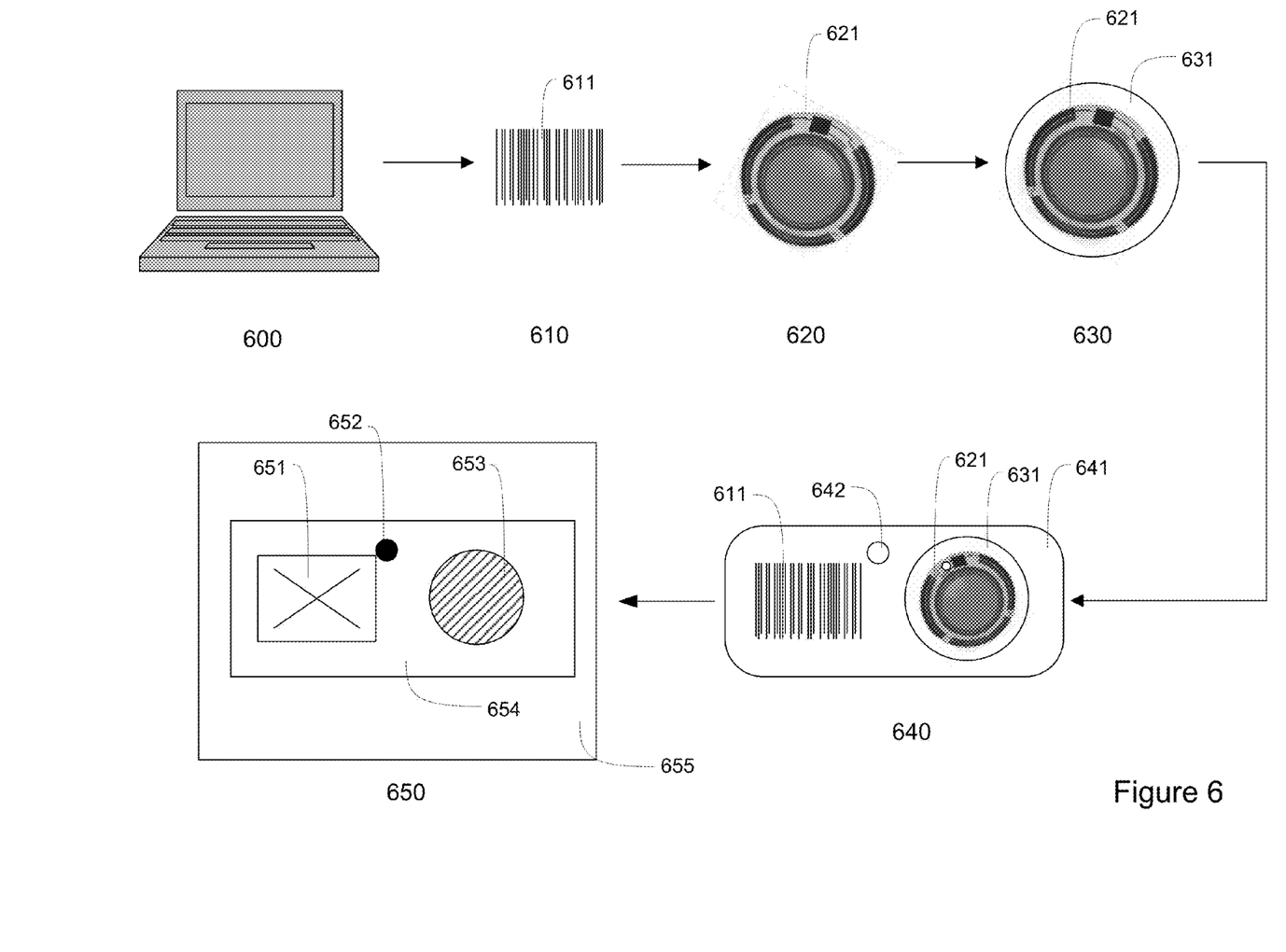
FIG. 6 illustrates an alternative process flowchart for programming an energizable Ophthalmic Lens.

Proceeding to FIG. 6, an alternate example of a process flow for assigning a SKU and programming an Ophthalmic Lens is illustrated. In some embodiments, an unprogrammed Media Insert 621 may be manufactured at 620 based on the programming parameters input at 600. At 610, a SKU and SKU barcode 611 may be generated based on the programming parameters. At 620, the unprogrammed Media Insert 621 may be assembled. An Ophthalmic Lens 631 with an unprogrammed Media Insert 621 may be assembled at 630 and included within a container 641 at 640. The container 641 may include an alignment feature 642 and the SKU barcode 611 associated with the programming parameters.

In some embodiments, the SKU 611 may be included on the container 641, such as, for example, where the Media Insert 621 is programmed while still sealed in the container 641. In some embodiments, the SKU 611 may be included on one or both of the Ophthalmic Lens 630 and the Media Insert 621, which may allow for programming after the Ophthalmic Lens 630 is removed from the sealed container 641.

In some embodiments, at 650, the Ophthalmic Lens 630 may be placed in a programming apparatus 655, for example, while still sealed within the container 641. In such aspects, an alignment feature 642 on the container 641 may interface with a complementary alignment feature 652 in a fitted cavity 654 within the programming apparatus 655, which may orient and secure the position of the Ophthalmic Lens 630 relative to the programming portion 653. A scanning portion 651 may scan the container 641 or the Ophthalmic Lens 630 for the associated SKU 611. A programming portion 653 may wirelessly program the Media Insert 621 based on that SKU 611.

Such an embodiment may be significant where the customization may require that the Media Insert 621 comprise specific components and where the programming may occur separately from the manufacturing process. Separating the programming of the Ophthalmic Lens 631 with the Media Insert 621 from the manufacturing process may allow for a wider range of programming options. As described with FIG. 3, a doctor, user, or anyone with access to the programming apparatus or SKU settings may set the programming parameters.

In some embodiments, the programming parameters may be adjusted after the manufacturing process. Such an embodiment may allow a user to order multiple Ophthalmic Lenses with unprogrammed Media Inserts without committing to a single set of programming parameters. This may be particularly preferable where the programming parameters may be or may need to be altered frequently.

For example, where a unique compound reacts with a constituent in the tear fluid, the reactants may be included during the manufacturing process, but the specific levels that may trigger a notification may be tailored through use of a programming apparatus. Similarly, where the programming parameters may be altered based on data collected by the Media Insert, a subsequently programmed Media Insert may require adjusted programming parameters.

Another example may include a cosmetic functionality where a user may select an embedded, static design and a limited number of colors. In some such embodiments, the same base design and colors may permit the user to choose a variety of permutations, each capable of providing a distinct appearance.

Processes

Proceeding to FIG. 7, an exemplary flowchart of method steps for manufacturing an energizable Ophthalmic Lens with a programmable Media Insert is illustrated. At 705, programming parameters may be uploaded into the manufacturing system, and at 710, a stock-keeping unit may be generated to uniquely identify the programming parameters and the corresponding energized Ophthalmic Lens.

In some embodiments, the manufacturing may be performed in separate processes or even separate facilities, and the step at 705 may be repeated for each process portion. In some such embodiments, the stock-keeping unit generated at 710 may be universal for each separate manufacturing process. A universal SKU may provide an effective method of ensuring the separately manufactured components are correctly assembled. For example, each component may include the SKU on some scannable surface.

In some embodiments, at 715, a processor may be programmed according to the programming parameters, wherein the processor may be included in a Media Insert. Programming the processor before encapsulating the electrical components within the Media Insert may not limit programming to wireless communication with the processor. Such an embodiment may not be preferable where the programming parameters are likely to change for an individual patient or where reprogramming an Ophthalmic Lens may be necessary.

At 720, the Media Insert may be assembled. In some embodiments, the Media Insert may comprise the processor electrically connected by conductive traces to a power source capable of providing power to an energization element, wherein the energization element may provide functionality to the energized Ophthalmic Lens. In embodiments where wireless communication may be significant, the Media Insert may further comprise one or more of a wireless transmitter, a wireless receiver, or a wireless sensor.

In some embodiments, the components within the Media Insert may be customizable, such as, for example, where the Media Insert may monitor a limited number of tear fluid constituents. The same Media Insert may be capable of monitoring temperature and pH within the ocular environment. In such embodiments, the assembly step at 720 may include selecting the customizable components based on the programming parameters. For example, specific reactants or binders may be indicative of a concentration of the monitored constituents.

At 725, the Media Insert may be assembled into an Ophthalmic Lens. In some embodiments, the Ophthalmic Lens may comprise a polymerized Reactive Monomer Mixture. In some embodiments, particularly where the Media Insert may be wirelessly programmed, the assembly with the Ophthalmic Lens may not impede or prevent wireless communication. Accordingly, where the polymerized RMM may inhibit wireless communication, the Media Insert may not be fully encapsulated within the Ophthalmic Lens. The assembly steps at 720 or 725 may include printing or embedding the SKU barcode on a surface of the Media Insert of the soft lens portion, which may be preferable where the Ophthalmic Lens may be wireless programmed.

The Ophthalmic Lens may be formed through a variety of methods, including, for example, injection molding or freeform techniques. Injection molding techniques may utilize a front curve mold piece and a back curve mold piece, wherein the Media Insert and a Reactive Monomer Mixture may be placed between the two mold pieces. The RMM may be polymerized between the mold pieces to encapsulate or at least secure the Media Insert to the Ophthalmic Lens.

Alternatively, freeform techniques may utilize actinic radiation to control polymerization on a voxel by voxel basis over a forming surface; wherein the actinic radiation may comprise a wavelength at least partially absorbed by the photoabsorptive component. In such embodiments, the RMM may comprise a photoabsorptive material. In some aspects, the Media Insert may be placed in or in contact with the RMM prior to polymerization, wherein exposure to the actinic radiation secures the position of the Media Insert in the Ophthalmic Lens. Alternatively, the Media Insert may be placed in contact with polymerized RMM, and the position may be secured by additional components, including, for example, alignment features or adhesives.

In some embodiments, at 730, the energizable Ophthalmic Lens may be packaged. The packaging may be particularly significant where the energizable Ophthalmic Lens may be programmed through a sealed container. A typical packaging for an Ophthalmic Lens may include a blister embodiment, wherein the blister comprises a plastic base and a sealing layer. The plastic base may include a reservoir portion capable of containing the Ophthalmic Lens in an aqueous solution. The assigned SKU barcode may be printed or embedded on a visible or scannable portion of the sealed container. The packaging at 730 may include a labeling process wherein some or all of the programming parameters are listed on the sealed container, for example.

Proceeding to FIG. 8, an exemplary flowchart of method steps for programming an energizable Ophthalmic Lens with a programmable Media Insert is illustrated. In such embodiments, the programming process may occur after the Media Insert is included in the Ophthalmic Lens. The programming may be directly transmitted to the Media Insert or indirectly through use of an overlay capable of programming the Media Insert. In some embodiments, the steps may be performed by a programming apparatus, which are illustrated for exemplary purposes. Other embodiments that may include manual performance of at least some of the steps are also within the scope of the inventive art.

At 805, the programming parameters may be received. In some embodiments, the programming parameters may be directly input to the programming apparatus or may be received from an external device, such as through an internet connection or through use of a universal serial bus. In some such embodiments, the programming apparatus may include a database of programming parameters organized, for example, by stock-keeping units.

In some embodiments, the programming apparatus may be capable of accessing and dispensing unprogrammed Ophthalmic Lenses or overlays. In such embodiments, at 810, the programming apparatus may select the specified unprogrammed Ophthalmic Lens or overlay, and at 815, the programming apparatus may place the Lens or overlay in proximity to the programming portion of the programming apparatus. In other embodiments, at 815, the programming apparatus may receive the unprogrammed Ophthalmic Lens or overlay, such as, for example, where a user or external mechanism may place the Lens or overlay.

In some embodiments, a stock-keeping unit (SKU) may be generated for each set of programming parameters. In some such embodiments, at 820, a SKU barcode may be scanned. The SKU barcode may be included on one or more of the overlay, the Ophthalmic Lens base, the Media Insert, or the container. Scanning the SKU barcode may provide a method of verifying the correct unprogrammed Ophthalmic Lens or overlay has been placed in the programming apparatus. Alternatively, the programming apparatus may access a database of programming parameters and may pull the parameters based on the SKU. In such embodiments, the step at 820 may prompt the step at 805, or the steps at 805 and 820 may occur concurrently.

At 825, the programming apparatus may wirelessly transmit the programming parameters to the overlay or to the Media Insert. In some aspects, the programming apparatus may be manually prompted to transmit. In other aspects, the programming apparatus may automatically transmit once the overlay or Ophthalmic Lens is placed in a predefined position in or relative to the programming apparatus.

In some embodiments, at 830, the programming apparatus may release the programmed overlay or Ophthalmic Lens. Alternatively, where the Ophthalmic Lens or overlay may not be secured in the programming apparatus, the release step at 830 may not be necessary. In embodiments with an overlay, at 835, the programming apparatus may optionally assemble the Ophthalmic Lens and place the programmed overlay in proximity to the Ophthalmic Lens base with the Media Insert. In other embodiments, the overlay may be manually combined with the Ophthalmic Lens base, such as by a user or an ophthalmologist.

Some aspects of programming may allow for adjustments to the programming parameters based on data collected by a programmed Media Insert, while the Ophthalmic Lens is located on the eye. In such embodiments, at 840, the programming apparatus may receive the Ophthalmic Lens after use, and at 845, the programming apparatus may wirelessly receive or upload data collected by the Media Insert. Similar to the step at 815, the Ophthalmic Lens may not be placed within the programming apparatus. In some such embodiments, at 845, the programming apparatus may be placed in proximity to the Ophthalmic Lens, or the Ophthalmic Lens may be placed in proximity to the programming apparatus.

At 850, the data may be transmitted to an external device, such as a computer, where the data may be reviewed, such as by an ophthalmologist. In some embodiments, at 855, the original programming parameters received at step 805 may be adjusted based on the received data. For example, the programming apparatus may comprise executable software capable of processing the received data relative to programming parameters. In such embodiments, the programming process may be repeated with the same or a second Ophthalmic Lens based on the adjusted programming parameters.

Materials for Insert Based Ophthalmic Lenses

In some embodiments, a lens type can be a lens that includes a silicone-containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

In some embodiments, the Ophthalmic Lens skirt, which sometimes may be called an insert encapsulating layer, that surrounds the insert may be comprised of standard hydrogel lens formulations. Exemplary materials with characteristics that may provide an acceptable match to numerous insert materials may include the Narafilcon family; including Narafilcon A and Narafilcon B. Alternatively, the Etafilcon family; including Etafilcon A may represent good exemplary material choices. A more technically inclusive discussion follows on the nature of materials consistent with the art herein; but it may be clear that any material which may form an acceptable enclosure or partial enclosure of the sealed and encapsulated inserts are consistent and included.

Suitable silicone containing components include compounds of Formula I where:

$R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another embodiment b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In one embodiment, where a silicone hydrogel lens is desired, the lens of the present invention will be made from a Reactive Mixture comprising at least about 20 and preferably between about 20 and 70% wt silicone containing components based on total weight of reactive monomer components from which the polymer is made.

In another embodiment, one to four $R^1$ comprises a vinyl carbonate or carbamate of the formula:

Formula II wherein: Y denotes O—, S— or NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris(trimethylsiloxy)silane]; 3-[tris(trimethylsiloxy)silyl]propyl allyl carbamate; 3-[tris(trimethylsiloxy)silyl]propyl vinyl carbamate; trimethylsilylethyl vinyl carbonate; trimethylsilylmethyl vinyl carbonate, and Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

Formulae IV-VI wherein:

D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$a$ is at least 1;

A denotes a divalent polymeric radical of formula:

Formula VII

$R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

Formula IX wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Formula X

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkages and crosslinkable monomers containing polyether and polysiloxanyl groups. Any of the foregoing polysiloxanes can also be used as the silicone-containing component in this invention.

CONCLUSION

The present invention, as described above and as further defined by the claims below, provides an apparatus for programming an energizable Ophthalmic Lens with a programmable Media Insert. In some embodiments, a Media Insert may be programmable to allow for further customization of the energized Ophthalmic Lens. The programming may occur after the electrical components have been encapsulated in the programmable Media Insert.

In some embodiments, the apparatus may wirelessly program the Media Insert after the Ophthalmic Lens has been fully assembled. Alternatively, the apparatus may indirectly program the Media Insert by wirelessly programming an overlay. The overlay may subsequently program the Media Insert when placed in proximity to the Media Insert, wherein the placing completes the assembly of the Ophthalmic Lens.

The invention claimed is:

1. A programming apparatus for programming a first energizable Ophthalmic Lens, the programming apparatus comprising:
   a programming portion capable of wirelessly programming a programmable Media Insert when the programming portion is located in proximity to a first energizable Ophthalmic Lens,
   wherein the first energizable Ophthalmic Lens comprises the programmable Media Insert and a soft lens base, wherein the soft lens base is in contact with at least a portion of the programmable Media Insert.

2. The programming apparatus of claim 1, further comprising a power source in electrical communication with the programming portion.

3. The programming apparatus of claim 1, further comprising a receiving portion, capable of receiving the first energizable Ophthalmic Lens.

4. The programming apparatus of claim 3, wherein the receiving portion further comprises an alignment feature, wherein the alignment feature is capable of orienting the first energizable Ophthalmic Lens with the programming portion.

5. The programming apparatus of claim 1, wherein the programming apparatus comprises a handheld device.

6. The programming apparatus of claim 1 further comprising:
   a dispensing portion, wherein the dispensing portion is capable of accessing a plurality of unprogrammed energizable Ophthalmic Lenses with programmable Media Inserts,
   wherein the first energizable Ophthalmic Lens comprises a selection from the plurality of unprogrammed energizable Ophthalmic Lenses, and
   wherein the dispensing portion is capable of placing the first energizable Ophthalmic Lens in proximity to the programming portion.

7. The programming apparatus of claim 1, wherein the programming apparatus comprises a portable device.

8. The programming apparatus of claim 1, wherein the programming portion comprises:
   a receiver capable of receiving programming parameter data;
   a transmitter capable of wirelessly transmitting a set of programming parameters to the programmable Media Insert; and
   a processor comprising executable software,
   wherein the processor is in logical communication with the receiver and the transmitter, and wherein the executable software is capable of storing the set of programming parameters.

9. The programming apparatus of claim 8, wherein the programming apparatus comprises a programming overlay capable of fitting over the first energizable Ophthalmic Lens, and wherein the programming overlay further comprises a soft lens portion capable of encapsulating the receiver, the transmitter, and the processor.

10. The programming apparatus of claim 8, wherein a stock-keeping unit comprises the set of programming parameters, and wherein the programming apparatus further comprises:
    a scanning portion in electrical communication with the receiver and the power source,
    wherein the scanning portion is capable of recognizing the stock-keeping unit and transmitting the set of programming parameters to the receiver.

11. The programming apparatus of claim 10, wherein the stock-keeping unit is identifiable by a stock-keeping unit barcode located on a surface of the first energizable Ophthalmic Lens or a surface of a container capable of holding the first energizable Ophthalmic Lens, and wherein the scanning portion comprises:
    a light source proximate to the stock-keeping unit barcode, wherein the light source is capable of directing light to the stock-keeping unit barcode, and wherein the surface is capable of reflecting the light; and
    a photodiode that is capable of measuring the intensity of the reflected light.

12. The programming apparatus of claim 11, wherein the light source comprises a laser.

13. The programming apparatus of claim 8, wherein the receiver is capable of logical communication with an external device.

14. The programming apparatus of claim 8, wherein the receiver comprises an input portion, wherein the input portion is capable of accepting the set of programming parameters.

15. The programming apparatus of claim 8, wherein the receiver is capable of wirelessly receiving predefined data from the programmable Media Insert of the first energizable Ophthalmic Lens, wherein the programmable Media Insert is capable of collecting the predefined data.

16. The programming apparatus of claim 15, wherein the executable software is capable of adjusting the set of programming parameters based on the predefined data.

17. The programming apparatus of claim 16, wherein the programming portion is capable of wirelessly programming a second energizable Ophthalmic Lens based on the adjusted set of programming parameters.

18. The programming apparatus of claim 16, wherein the programming portion is capable of wirelessly reprogramming the first energizable Ophthalmic Lens based on the adjusted set of programming parameters.

19. The programming apparatus of claim 8, wherein the programming portion is capable of programming the programmable Media Insert when the energizable Ophthalmic Lens is located within a sealed container, the sealed container comprising:
- a reservoir of aqueous solution capable of maintaining a specified level of hydration in the energized Ophthalmic Lens;
- a rigid portion comprising a recess capable of containing the reservoir and the energized Ophthalmic Lens; and
- a sealing layer covering the recess, wherein the sealing layer is capable of limiting exposure of the first energizable Ophthalmic Lens to predefined ambient conditions.

20. The programming apparatus of claim 19, wherein the sealing layer is permeable to a wireless transmission between the transmitter and the programmable Media Insert.

* * * * *